United States Patent [19]

Hamprecht et al.

[11] Patent Number: 5,030,727
[45] Date of Patent: Jul. 9, 1991

[54] PREPARATION OF THIAZOLO (2,3-B) ZUINAZOLONES

[75] Inventors: Gerhard Hamprecht, Weinheim; Guenther Seybold, Neuhoren; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 508,495

[22] Filed: Apr. 12, 1990

Related U.S. Application Data

[60] Continuation of Ser. No. 333,797, Apr. 5, 1989, abandoned, which is a division of Ser. No. 106,645, Oct. 9, 1987, abandoned.

[30] Foreign Application Priority Data

Oct. 10, 1986 [DE] Fed. Rep. of Germany ....... 3634532

[51] Int. Cl.$^5$ .................. C07D 239/70; A01N 43/02
[52] U.S. Cl. ........................................ 544/250; 71/90
[58] Field of Search ............................. 544/250; 71/90

[56] References Cited

U.S. PATENT DOCUMENTS

| | | | |
|---|---|---|---|
| 4,168,380 | 9/1979 | LeMahieu | 544/250 |
| 4,282,360 | 8/1981 | LeMahieu | 544/250 |
| 4,443,451 | 4/1984 | Kennis et al. | 544/48 |
| 4,486,221 | 12/1984 | Seybold et al. | 71/90 |
| 4,548,938 | 10/1985 | Kennis et al. | 544/250 |
| 4,783,469 | 11/1958 | Campbell et al. | 544/250 |

FOREIGN PATENT DOCUMENTS

| | | | |
|---|---|---|---|
| 0078002 | 5/1983 | European Pat. Off. | 544/250 |
| 20528 | 12/1986 | European Pat. Off. | 544/250 |
| 1572707 | 7/1980 | United Kingdom. | |

OTHER PUBLICATIONS

C. A. vol. 52, p. 5383 d.
Tetrah. 15, 53–59 (1961), Sharma et al.
J. Org. Chem. 27, 2672, 73 (1962).
Morrison and Boyd, "Organic Chemistry" 3rd, Ed. 1978, p. 829.

Primary Examiner—Alan L. Rotman
Assistant Examiner—Celia Chang
Attorney, Agent, or Firm—Keil & Weinkauf

[57] ABSTRACT

The process of manufacturing thiazolo-(2,3-b)-quinoazolones of the formula I

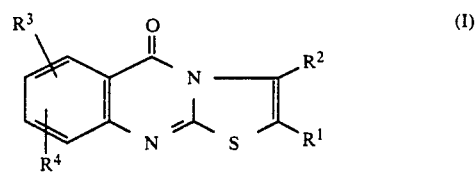

where $R^1$, $R^2$, $R^3$ and $R^4$ are defined in the disclosure, wherein either a) an anthranilamide derivative of the formula II

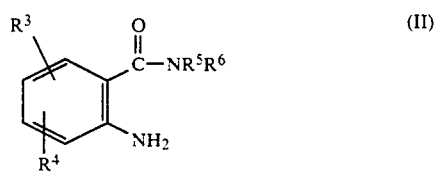

where $R^5$ and $R^6$ are hydrogen or $C_1$–$C_4$-alkyl, is reacted with a thiazole derivative of the formula III

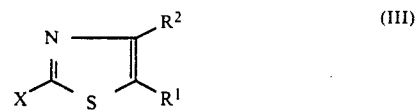

where X is fluorine, chlorine, bormine, alkylsulfonyl or arylsulfonyl, or b) for certain radicals $R^{4'}$ from the group $R^4$- a thiazolo-(2,3-b)-quinazolone of the general formula IV

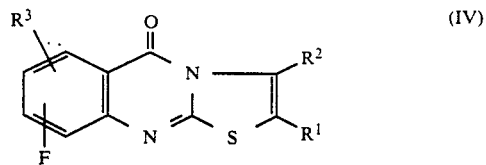

is reacted with a nucleophile $R^{4'}$-H, where $R^{4'}$ is alkoxy, alkylthio or unsubstituted or halogen-, alkyl-, haloalkyl-, nitro- or alkoxy-substituted phenoxy or thiophenyl, or an alkali metal, alkaline earth metal or ammonium salt of an alcohol.

6 Claims, No Drawings

PREPARATION OF THIAZOLO (2,3-B) ZUINAZOLONES

This application is a continuation of Ser. No. 333,797, filed Apr. 5, 1989, which is a divisional of Ser. No. 106,645, filed Oct. 9, 1987 both now abandoned.

The present invention relates to a novel process for preparing a thiazolo(2,3-b)quinoazolone of the general formula I

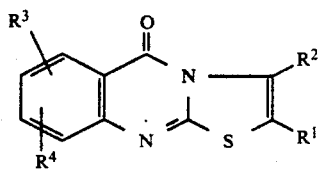

where $R^1$, $R^2$, $R^3$ and $R^4$ are each hydrogen, halogen, nitro, cyano, alkyl, haloalkyl, cycloalkyl, alkoxy, alkylthio, alkanoylamino, haloalkanoylamino, carboxyl, carbamoyl, dialkylcarboxamido, alkoxycarbonylalkyl, unsubstituted or alkoxy-substituted alkoxycarbonyl, alkylsulfonyl, phenylsulfonyl, sulfamoyl, alkylaminosulfonyl, alkylsulfonylamino, unsubstituted or halogen-, alkyl-, haloalkyl-, nitro- or alkoxy-substituted phenyl, phenoxy or thiophenyl or unsubstituted or halogen- or alkyl-substituted hetaryl.

The present invention also relates to novel thiazolo(2,3-b)quinoazolones of the general formula Ia

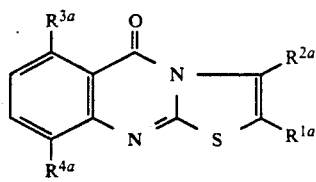

where $R^{1a}$ and $R^{2a}$ are each hydrogen, halogen, nitro, cyano, $C_1$–$C_{20}$-alkyl, $C_1$–$C_{20}$-haloalkyl, $C_3$–$C_8$-cycloalkyl, $C_1$–$C_{20}$-alkoxy, $C_1$–$C_{20}$-alkylthio, $C_1$–$C_{20}$-alkanoyl amino, $C_1$–$C_{20}$-haloalkanoylamino, carboxyl, carbamoyl, $C_3$–$C_{20}$-dialkylcarboxamido, $C_3$–$C_{20}$-alkoxycarbonylalkyl, unsubstituted or $C_1$–$C_{20}$-alkoxy-substituted $C_2$–$C_{20}$-alkoxycarbonyl, $C_1$–$C_{20}$-alkylsulfonyl, phenylsulfonyl, sulfamoyl, $C_1$–$C_{20}$-alkylaminosulfonyl, $C_1$–$C_{20}$-alkylsulfonylamino, unsubstituted or halogen-, $C_1$–$C_{20}$-alkyl-, $C_1$–$C_{20}$-haloalkyl, nitro- or $C_1$–$C_{20}$-alkoxy-substituted phenyl, phenoxy or thiophenyl or unsubstituted or halogen- or $C_1$–$C_{20}$-alkyl-substituted hetaryl, $R^{3a}$ is hydrogen, chlorine, bromine, carboxyl, $C_1$–$C_4$-alkyl, $C_1$–$C_4$-alkoxy, $C_1$–$C_4$-alkylthio, unsubstituted or halogen-, methyl-, trifluoromethyl-, nitro- or methoxy-substituted phenoxy or thiophenyl, and $R^{4a}$ is one of $R^{3a}$ or fluorine, or salts of these thiazolo(2,3-b)quinazolones, except 6-chloro-3-methyl-5H-thiazolo(2,3-b)quinolin-5-one, 9-chloro-3-methyl-5H-thiazolo(2,3-b)quinolin-5-one, 9-fluoro-5H-thiazolo(2,3-b)quinolin-5-one, 9-fluoro-3-methyl-2-methoxycarbonyl-5-thiazolo(2,3-b)quinoazolin-5-one, 2,6-dichloro-5H-thiazolo(2,3-b)quinolin-5-one, 2,6-dimethyl-5H-thiazolo(2,3-b)quinolin-5-one, and also those compounds Ia where $R^{3a}$ and $R^{4a}$ are each hydrogen. The present invention further relates to the use of the novel compounds Ia as herbicides and to mixtures and agents containing same to control undesirable plant growth and to regulate plant growth.

German Laid-Open Application DOS 3,142,727 discloses a process for preparing the thiazolo(2,3-b)quinazolones I by reacting the corresponding anthranilic acids and their alkyl esters II with the corresponding thiazoles III according to the scheme

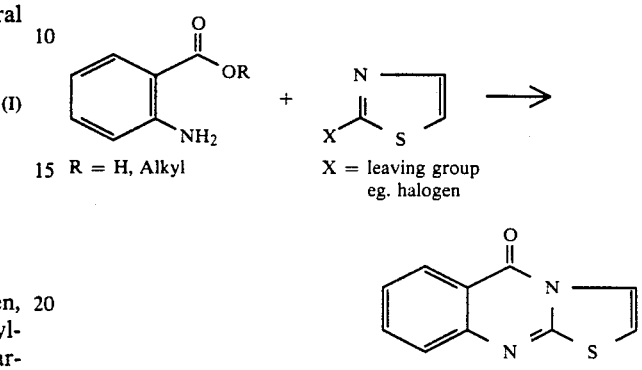

However, this process does not produce a satisfactory result in every case, in particular in the case of preparing these compounds I with substitutes in the 6- and/or 9-position.

It is an object of the present invention to remedy this disadvantage and to provide new active herbicides.

We have found that this object is achieved with a process for preparing compounds I, which comprises reacting a) either an anthranilamide derivative of the general formula II

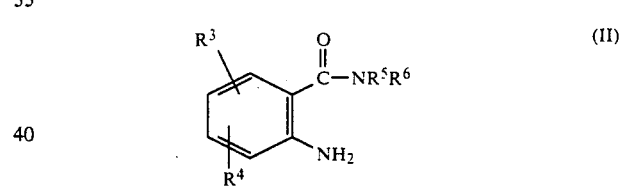

where $R^5$ and $R^6$ are each hydrogen or $C_1$–$C_4$-alkyl, with a thiazole derivative of the general formula III

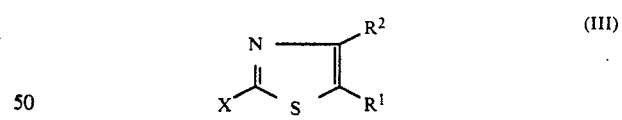

where X is fluorine, chlorine, bromine, alkylsulfonyl or arylsulfonyl, or b) for the case of certain radicals $R^{4'}$ of the group $R^4$, a thiazolo(2,3-b)quinazolone of the general formula IV

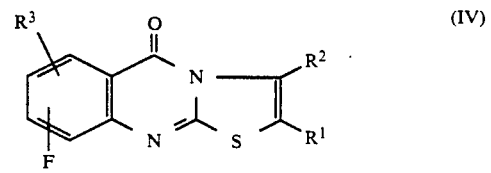

with a nucleophile $R^{4'}$-M, where $R^{4'}$ is alkoxy, alkylthio or unsubstituted or halogen-, alkyl-, haloalkyl-, nitro- or alkoxy-substituted phenoxy or thiophenyl and M is hydrogen or an alkali metal, alkaline earth metal or ammonium cation.

We have also found the novel thiazolo(2,3-b)quinazolones Ia defined at the beginning. We have also found that these compounds Ia are suitable for use as herbicides.

We have further found processes and agents for controlling undesirable plant growth and for regulating plant growth.

The processes for preparing the compounds I can be put into effect in the form of the following methods:

a) Reaction of an anthranilic acid derivative with a thiazole derivative.

The anthranilamide derivatives of the formula II used as starting materials and the thiazole derivatives of the formula III are either known or can be prepared in a conventional manner (J. Amer. Chem. Soc. 74 (1952), 1719; J. Sci. Ind. Res. 16 B (1957), 411 (CA. 52, 5383 d)).

If for example 6-methylanthranilamide and 2-chlorothiazole are the starting materials used, the course of the reaction can be represented by the following equation:

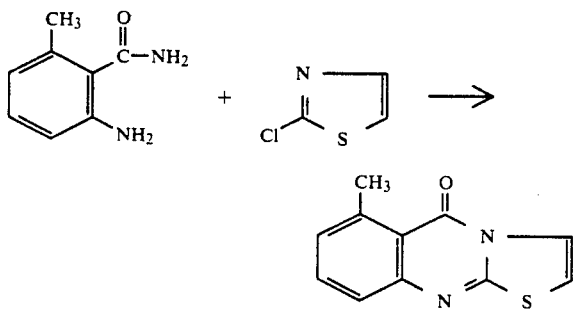

The reaction of the anthranilamide derivative of the formula II with the thiazole derivative of the formula III can be carried out at from 100° to 200° C., preferably at from 130° to 170° C. Advantageously, the thiazole is presented in an inert solvent or preferably in the melt, the anthranilamide is added and the reaction is then carried out for from 30 minutes to 12 hours. However, it is also possible first to present the anthranilamide in a solvent, to add the thiazole and to carry out the reaction as described. The reactants can be used in an approximately stoichiometric ratio. No addition of acid is necessary. Suitable inert solvents are halogenated hydrocarbons such as dichlorobenzene and trichlorobenzene, polyhydric alcohols such as glycol, ethylglycol and butylglycol, esters such as methylglycol acetate, sulfones such as sulfolane, phenol and phenol derivatives such as cresols or chlorophenols, or dimethylformamide. Mixtures of these solvents can also be used.

The reaction can be carried out continuously or batchwise at from 1 to 10 bar.

The reaction mixture can be worked up by stirring and washing with dilute sodium carbonate or ammonia solution and/or by briefly heating to the boil in an alcohol and then filtering off with suction. The end products thus obtained are already sufficiently pure for use as herbicides, for example. Of course, if required they can be further purified, for example for recrystallization or chromatography.

b) Reaction of a fluorothiazolo(2,3-b)quinoazolone with a nucleophile.

The reaction of a fluorothiazolo(2,3-b)quinoazolone of the formula IV with the nucleophile $R^{4'}$-M where $R^{4'}$ is alkoxy, alkylthio or unsubstituted or halogen-, alkyl-, haloalkyl-, nitro- or alkoxy-substituted phenoxy or thiophenyl and M is hydrogen or an alkali metal, alkaline earth metal or ammonium cation

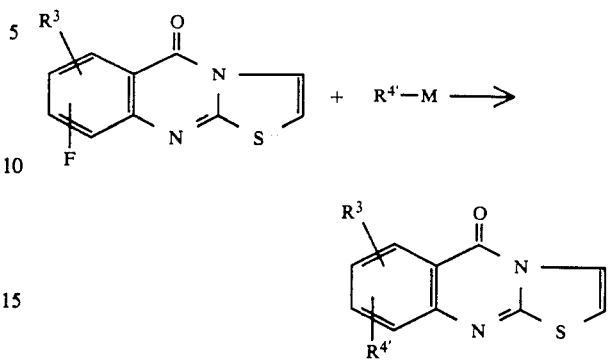

is carried out at from 40° to 200° C., out preferably at from 70° to 140° C. Preferred nucleophiles are methanol, ethanol, n-propanol, isopropanol, n-butanol, sec.-butanol, isobutanol, tert.-butanol, methylmercaptan, ethylmercaptan, n-propylmercaptan, isopropylmercaptan, n-butylmercaptan, isobutylmercaptan, sec.-butylmercaptan, tert.butylmercaptan, phenol, thiophenol, 2-, 3- and 4-chlorophenol, 2-, 3- and 4-chlorothiophenol, 2,4- and 3,4-dichlorophenol, 2,4- and 3,4-dichlorophenol, 2,4- and 3,4-dichlorothiophenol, 2-, 3- and 4-cresol, 2-, 3- and 4-thiocresol, 2-, 3- and 4-nitrophenol, 2-, 3- and 4-nitrothiophenol, 2-, 3- and 4-methoxyphenol, 2-, 3- and 4-methoxythiophenol, 2-chloro-4-trifluoromethylphenol, 2-chloro-4-trifluoromethylthiophenol, 3-chloro-4-methoxyphenol, 3-chloro-4-methoxythiophenol, 2-chloro-4-methoxyphenol, 2-chloro-4-methoxythiophenol and alkali metal salts thereof. Advantageously, the thiazolo(2,3-b)quinazolone of the formula Ia is presented in an inert solvent, the nucleophile is then added, and the reaction is then carried out for from 30 minutes to 10 hours. However, it is also possible to present the salt of the nucleophile in a solvent and to add the thiazolo(2,3-b)quinazolone. To bind any acid formed, it is possible to use the customary basic compounds. The reactants are likewise used in an approximately stoichiometric ratio. The reaction is advantageously carried out in the presence of a solvent. Possibilities are hydrocarbons such as benzene, toluene, cyclohexane and paraffin fractions such as petroleum ether, halohydrocarbons such as 1,1- or 1,2-dichloroethane, 1,1,1- or 1,1,2-trichloroethane, chlorobenzene, the dichlorobenzenes and the chlorotoluenes, nitro compounds such as nitrobenzene and nitroethane, nitriles such as acetonitrile, butyronitrile and isobutyronitrile, ethers such as dioxane, ester such as ethyl acetate and isobutyl acetate or amides such as formamide, methylformamide and dimethylformamide. Advantageously, the solvent is used in an amount of from 100 to 2000% by weight, preferably from 500 to 1500% by weight, based on the starting material IV.

The reaction can otherwise be carried out and worked up as described under a).

The salts of the thiazolo(2,3-b)quinazolones are obtained by protonation with the corresponding acids in the presence of an inert solvent such as, for example, tetrahydrofuran, dioxane, tert.-butyl methyl ether, methylene chloride or acetonitrile.

The salts can be formed with inorganic acids, for example hydrochloric acid, hydrobromic acid, hydrofluoric acid, sulfuric acid, phosphoric acid or perchloric acid, or organic acids, for example monochloroacetic acid, dichloroacetic acid, trichloroacetic acid or trifluoroacetic acid.

Of the compounds I, preference is given to those where $R^1$, $R^2$, $R^3$ and $R^4$ each have the following meanings: hydrogen, halogen, such as fluorine, chlorine, bromine or iodine, nitro, cyano, $C_1$–$C_{12}$-alkyl such as methyl, ethyl, n-, iso-propyl, n-, iso-, tert.-butyl, pentyl, hexyl, heptyl, octyl, nonyl, decyl, dodecyl, preferably $C_1$–$C_9$-alkyl, in particular $C_1$–$C_4$-alkyl, $C_1$–$C_4$-haloalkyl such as chloromethyl, fluoromethyl, difluoromethyl, trichloromethyl, trifluoro-methyl, pentafluoroethyl, 2-chloro-1,1,2,2-tetrafluoro-ethyl, nonafluoro-n-butyl, $C_3$–$C_6$-cycloalkyl such as cyclopropyl, cyclopentyl, cyclohexyl, $C_1$–$C_9$-alkoxy such as methoxy, ethoxy, n-, iso-propoxy, n-, iso-, tert.-butoxy, hexoxy, octyloxy, nonyloxy, preferably $C_1$–$C_6$-alkoxy, in particular $C_1$–$C_4$-alkoxy, $C_1$–$C_9$-alkylthio such as methylthio, ethylthio, n-, iso-propylthio, n-, iso-, tert.-butylthio, pentylthio, hexylthio, heptylthio, octylthio, nonylthio, preferably $C_1$–$C_6$-alkylthio, in particular $C_1$–$C_4$-alkylthio, $C_2$–$C_5$-alkanoylamino or halo-alkanoylamino such as acetylamino, chloroacetylamino, trifluoroacetylamino, propionylamino, 2-chloropropionylamino, carboxyl, carbamoyl, dialkylcarboxamido with $C_1$–$C_4$-alkyl, e.g. N,N-dimethylcarboxamido, N,N-diethylcarboxamido, N,N-di-n-butylcarboxamido, $C_1$–$C_4$-alkoxycarbonyl such as methoxycarbonyl, ethoxycarbonyl, n-propoxycarbonyl, tert.-butoxycarbonyl, isobutoxycarbonyl, $C_3$–$C_6$-alkoxycarbonylalkyl such as methoxycarbonylmethyl, ethoxycarbonylmethyl, n-butoxycarbonylmethyl, $C_3$–$C_7$-alkoxyalkoxycarbonyl such as 2-methoxyethoxycarbonyl, ethoxymethoxycarbonyl, 2-ethoxyethoxycarbonyl, $C_1$–$C_4$-alkylsulfonyl such as methylsulfonyl, ethylsulfonyl, isopropylsulfonyl, n-butyl-sulfonyl, phenylsulfonyl, sulfamoyl, $C_1$–$C_4$-alkylaminosulfonyl such as methyl-/aminosulfonyl, isopropylaminosulfonyl, n-butylaminosulfonyl, $C_1$–$C_4$-alkylsulfonylamino such as methylsulfonylamino, isopropylsulfonylamino, isobutylsulfonylamino, phenyl, phenoxy, thiophenyl, halogen-, $C_1$–$C_8$-alkyl-, $C_1$–$C_8$-haloalkyl-, nitro- or $C_1$–$C_8$-alkoxy-substituted phenyl, phenoxy or thiophenyl, such as 2-, 3- or 4-chlorophenyl, 2,4-and 3,4-dichlorophenyl, 2-, 3- and 4-tolyl, 2,4-xylyl, 2-, 3- and 4-trifluoromethylphenyl, 2-chloro-4-trifluoromethylphenyl, 2-, 3- and 4-nitrophenyl, 2-, 3- and 4-methoxyphenyl, 2-, 3- and 4-chlorophenoxy, 2,4- and 3,4-dichlorophenoxy, 2-, 3- and 4-cresoxy, 2-chloro-4-trifluoromethylphenoxy, 2-chloro-4-methoxyphenoxy, 2-, 3- and 4-nitrophenoxy, 2-, 3- and 4-methoxyphenoxy, 3-chloro-4-methoxyphenoxy, 2-, 3- and 4-chlorophenylthio, 2,4- and 3,4-dichlorophenylthio, 2-, 3- and 4-methylphenyl-thio, 2-chloro-4-trifluoromethylphenylthio, 2-chloro-4-methoxyphenylthio, 2-, 3- and 4-nitrophenylthio, 2-, 3- and 4-methoxyphenylthio, 3-chloro-4-methoxyphenylthio, hetaryl such as pyrid-2-yl, pyrid-3-yl, pyrid-4-yl, thien-2-yl, thien-3-yl, fur-2-yl, fur-3-yl, benzimidazol-2-yl and halogen- or $C_1$–$C_4$-alkyl-substituted hetaryl, such as 3-chloropyrid-6-yl, 2-methylfur-5-yl, 2-methylthien-5-yl and pyrimid-4-yl.

X is the formula III is preferably chlorine or bromine.

Of the novel compounds Ia, preference is given to those where $R^{1a}$, $R^{2a}$ each have the meanings of $R^1$ and $R^2$ and where $R^{3a}$ is hydrogen, chlorine or bromine, carboxyl, alkyl of 1 to 3 carbon atoms such as methyl, ethyl, n-propyl, isopropyl, alkoxy of 1 to 3 carbon atoms such as methoxy, ethoxy, n-propoxy, isopropoxy, alkylthio of 1 to 3 carbon atoms such as methylthio, ethylthio, n-propylthio, isopropylthio, unsubstituted or halogen-, methyl- tri-fluoromethyl-, nitro- or methoxy-substituted phenoxy, 2-, 3- or 4-chlorophenoxy, 2,4- or 3,4-dichlorophenoxy, 2-, 3- or 4-cresoxy, 2-chloro-4-trifluoromethylphenoxy, 2-chloro-4-methoxyphenoxy, 2-, 3- and 4-nitrophenoxy, 2-, 3- or 4-methoxyphenoxy, 3-chloro-4-methoxyphenoxy, thiophenyl such as phenylthio, 2-, 3- or 4-chlorophenylthio, 2,4- or 3,4-dichlorophenylthio, 2-, 3- or 4-methylphenylthio, 2-chloro-4-trifluoromethylphenylthio, 2-chloro-4-methoxyphenylthio, 2-, 3- or 4-nitrophenylthio, 2-, 3- or 4-methoxyphenylthio, 3-chloro-4-methoxyphenylthio and $R^{4a}$ is fluorine or one of $R^{3a}$, or to salts of these thiazolo-(2,3-b)-quinazolones, except 6-chloro-3-methyl-5H-thiazolo-(2,3-b)-quinazolin-5-one, 9-chloro-3-methyl-5H-thiazolo-(2,3-b)-quinazolin-5-, 9-fluoro-5-thiazolo(2,3-b)quinazoline-5-one, 9-fluoro-3-methyl-2-methoxycarbonyl-5H-thiazolo(2,3-b)quinazolin-5-one, 2,6-dichloro-5-thiazolo(2,3-b)quinazoline, 2,6-dimethyl-5H-quinazolin-5-one and those compounds Ia where $R^{3a}$ and $R^{4a}$ are both hydrogen.

Particular preference is given to compounds Ia where $R^{1a}$ and $R^{2a}$ are each hydrogen, chlorine or methyl and $R^{3a}$ and $R^{4a}$ are each hydrogen, methyl, halogen, carboxyl, $C_1$–$C_4$-alkoxy, $C_1$–$C_4$-alkylthio or unsubstituted or halogen-, methyl-, trifluoromethyl-, nitro- or methoxy-substituted phenoxy or phenylthio, or salts thereof, except 6-chloro-3-methyl-5H-thiazolo(2,3-b)quinazolin-5-one, 9-chloro-3-methyl-5-thiazolo(2,3-b)quinazolin-5-one, 9-fluoro-5H-thiazolo(2,3-b)quinazolin-5-one, 9-fluoro-3-methyl-2-methoxycarbonyl-5H-thiazolo(2,3-b)quinazolin-5-one, 2,6-dichloro-5H-thiazolo(2,3-b)quinazolin-5-one, 2,6-dimethyl-5H-thiazolo(2,3-b)quinazolin-5-one, and those compounds Ia where $R^{3a}$ and $R^{4a}$ are both hydrogen.

Very particularly preferred compounds of the formula Ia are those where $R^{1a}$ is hydrogen or chlorine, $R^{2a}$ is hydrogen, chlorine or methyl, $R^{3a}$ is hydrogen, chlorine, bromine, carboxy, $C_1$–$C_4$-alkyl, $C_1$–$C_4$-alkoxy, $C_1$–$C_4$-alkylthio or unsubstituted or halogen-, methyl-, trifluoromethyl-, nitro- or methoxy-substituted phenoxy or phenylthio and $R^{4a}$ is hydrogen, except compounds Ia where $R^{3a}$ and $R^{4a}$ are both hydrogen.

Examples of novel compounds Ia are:

| Compound No. | |
|---|---|
| 1 | 9-chloro-5H-thiazolo(2,3-b)quinazolin-5-one |
| 2 | 6-fluoro-5H-thiazolo(2,3-b)quinazolin-5-one |
| 3 | 6-methyl-5H-thiazolo(2,3-b)quinazolin-5-one |
| 4 | 2-chloro-6-methyl-5H-thiazolo(2,3-b)quinazolin-5-one |
| 5 | 6-methylmercapto-5H-thiazolo(2,3-b)quinazolin-5-one |
| 6 | 6-phenoxy-5H-thiazolo(2,3-b)quinazolin-5-one |
| 7 | 6-chloro-5H-thiazolo(2,3-b)quinazolin-5-one |
| 8 | 6-bromo-5H-thiazolo(2,3-b)quinazolin-5-one |
| 9 | 9-fluoro-5H-thiazolo(2,3-b)quinazolin-5-one |
| 10 | 9-bromo-5H-thiazolo(2,3-b)quinazolin-5-one |
| 11 | 6,9-dichloro-5H-thiazolo(2,3-b)quinazolin-5-one |
| 12 | 9-methyl-5H-thiazolo(2,3-b)quinazolin-5-one |
| 13 | 6-chloro-3-methyl-5H-thiazolo(2,3-b)quinazolin-5-one |
| 14 | 6-chloro-2-methyl-5H-thiazolo(2,3-b)quinazolin-5-one |
| 15 | 9-fluoro-3-methyl-5H-thiazolo(2,3-b)quinazolin-5-one |
| 16 | 9-fluoro-2-methyl-5H-thiazolo(2,3-b)quinazolin-5-one |

| Compound No. | |
|---|---|
| 17 | 3,9-dimethyl-5H-thiazolo(2,3-b)quinazolin-5-one |
| 18 | 2,9-dimethyl-5H-thiazolo(2,3-b)quinazolin-5-one |
| 19 | 3,6-dimethyl-5H-thiazolo(2,3-b)quinazolin-5-one |
| 20 | 6-bromo-3-methyl-5H-thiazolo(2,3-b)quinazolin-5-one |
| 21 | 6-methoxy-2-methyl-5H-thiazolo(2,3-b)quinazolin-5-one |
| 22 | 2-chloro-6-methoxy-5H-thiazolo(2,3-b)quinazolin-5-one |
| 23 | 6-methoxy-3-methyl-5H-thiazolo(2,3-b)quinazolin-5-one |
| 24 | 2,3-dichloro-6-methoxy-5H-thiazolo(2,3-b)quinazolin-5-one |
| 25 | 2,3,6-trichloro-5H-thiazolo(2,3-b)quinazolin-5-one |
| 26 | 2,3-dichloro-6-fluoro-5H-thiazolo(2,3-b)quinazolin-5-one |
| 27 | 2,3-dichloro-6-methyl-5H-thiazolo(2,3-b)quinazolin-5-one |
| 28 | 2,3-dichloro-9-methyl-5H-thiazolo(2,3-b)quinazolin-5-one |
| 29 | 2,3,9-trichloro-5H-thiazolo(2,3-b)quinazolin-5-one |
| 30 | 2,3-dichloro-9-methoxy-5H-thiazolo(2,3-b)quinazolin-5-one |
| 31 | 2,3-dichloro-9-fluoro-5H-thiazolo(2,3-b)quinazolin-5-one |
| 32 | 2-chloro-9-methoxy-5H-thiazolo(2,3-b)quinazolin-5-one |
| 33 | 9-methoxy-3-methyl-5H-thiazolo(2,3-b)quinazolin-5-one |
| 34 | 2,3-dichloro-9-methoxy-5H-thiazolo(2,3-b)quinazolin-5-one |
| 35 | 6,9-dimethyl-5H-thiazolo(2,3-b)quinazolin-5-one |
| 36 | 6-chloro-9-methyl-5H-thiazolo(2,3-b)quinazolin-5-one |
| 37 | 9-chloro-6-methyl-5H-thiazolo(2,3-b)quinazolin-5-one |
| 38 | 6-chloro-3,9-dimethyl-5H-thiazolo(2,3-b)quinazolin-5-one |
| 39 | 6,9-dichloro-3-methyl-5H-thiazolo(2,3-b)quinazolin-5-one |
| 40 | 2,6,9-trichloro-5H-thiazolo(2,3-b)quinazolin-5-one |
| 41 | 3,6-dimethyl-5H-thiazolo(2,3-b)quinazolin-5-one |
| 42 | 2-chloro-6-methylmercapto-5H-thiazolo(2,3-b)quinazolin-5-one |
| 43 | 6-ethoxy-5H-thiazolo(2,3-b)quinazolin-5-one |
| 44 | 6-ethoxy-3-methyl-5H-thiazolo(2,3-b)quinazolin-5-one |
| 45 | 6-isopropoxy-5H-thiazolo(2,3-b)quinazolin-5-one |
| 46 | 9-ethoxy-5H-thiazolo(2,3-b)quinazolin-5-one |
| 47 | 9-ethoxy-3-methyl-5H-thiazolo(2,3-b)quinazolin-5-one |
| 48 | 9-methoxy-5H-thiazolo(2,3-b)quinazolin-5-one |
| 49 | 6-methoxy-5H-thiazolo(2,3-b)quinazolin-5-one |
| 50 | 6-phenylmercapto-5H-thiazolo(2,3-b)quinazolin-5-one |
| 51 | 6-(2,4-dichlorophenoxy)-5H-thiazolo(2,3-b)quinazolin-5-one |
| 52 | 6-(2-chloro-4-trifluoromethylphenoxy)-5H-thiazolo(2,3-b)quinzolin-5-one |
| 53 | 6-p-nitrophenoxy-5H-thiazolo(2,3-b)quinazolin-5-one |
| 54 | 6-p-methoxyphenoxy-5H-thiazolo(2,3-b)quinazolin-5-one |
| 55 | 6-p-methylphenylmercapto-5H-thiazolo(2,3-b)quinazolin-5-one |
| 56 | 6-(2,4-dichlorophenylmercapto)-5H-thiazolo(2,3-b)quinazolin-5-one |
| 57 | 6-carboxy-3-methyl-5H-thiazolo(2,3-b)quinazolin-5-one |
| 58 | 2-methyl-5H-thiazolo(2,3-b)quinazolin-5-one |
| 59 | 6-fluoro-2-methyl-5H-thiazolo(2,3-b)quinazolin-5-one |
| 60 | 2-bromo-5H-thiazolo(2,3-b)quinazolin-5-one |
| 61 | 3-methyl-6-trifluoromethyl-5H-thiazolo(2,3-b)quinazolin-5-one |
| 62 | 6-trifluoromethyl-5H-thiazolo(2,3-b)quinazolin-5-one |
| 63 | 9-trifluoromethyl-5H-thiazolo(2,3-b)quinazolin-5-one |
| 64 | 9-chloro-3-methyl-5H-thiazolo(2,3-b)quinazolin-5-one |
| 65 | 2,6-dimethyl-5H-thiazolo-(2,3-b)quinazolin-5-one |
| 66 | 2-bromo-3,6-dimethyl-5H-thiazolo-(2,3-b)quinazol-5-one |
| 67 | 2-bromo-6-chloro-3-methyl-5H-thiazolo(2,3-b)quinazolin-5-one |
| 68 | 2-bromo-3,9-dimethyl-5H-thiazolo-(2,3-b)quinazolin-5-one |
| 69 | 2-bromo-9-chloro-3-methyl-5H-thiazolo(2,3-b)quinazolin-5-one |
| 70 | 2,6-dichloro-3-methyl-5H-thiazolo(2,3-b)quinazolin-5-one |
| 71 | 2,3,6-trimethyl-5H-thiazolo(2,3-b)quinazolin-5-one |
| 72 | 6-chloro-2,3-dimethyl-5H-thiazolo(2,3-b)quinazolin-5-one |
| 73 | 2,3,9-trimethyl-5H-thiazolo(2,3-b)quinazolin-5-one |
| 74 | 9-chloro-2,3-dimethyl-5H-thiazolo-(2,3-b)quinazolin-5-one |
| 75 | 2,3-dimethyl-6-fluoro-5H-thiazolo(2,3-b)quinazolin-5-one |
| 76 | 2,3-dimethyl-6-methoxy-5H-thiazolo(2,3-b)quinazolin-5-one |
| 77 | 2-methoxy-5H-thiazolo(2,3-b)quinazolin-5-one |
| 78 | 6-chloro-2-methoxy-5H-thiazolo(2,3-b)quinazolin-5-one |
| 79 | 2-methoxy-9-methyl-5H-thiazolo(2,3-b)quinazolin-5-one |
| 80 | 2-bromo-9-methoxy-3-methyl-5H-thiazolo(2,3-b)-quinazolin-5-one |
| 81 | 2,3-dimethyl-9-methoxy-5H-thiazolo(2,3-b)-quinazolin-5-one |
| 82 | 2-bromo-6-methyl-5H-thiazolo(2,3-b)-quinazolin-5-one |

The action of some of the compounds of the formula Ia was investigated on the following plants in the greenhouse:

*Amaranthus retroflexus, Avena sativa, Centaurea cyanus, Chenopodium album, Cyperus esculentus, Cyperus iria, Digitaria sanguinalis, Echinochloa crus-galli, Euphorbia heterophylla, Galium aparine,* Ipomoea spp., *Mercurialis annua, Sesbania exaltata, Setaria italica, Sinapis alba, Solanum nigrum, Sorghum bicolor, Triticum aestivum,* and *Zea mays.*

The thiazolo-(2,3-b)-quinazolone derivatives of the formula Ia, or growth-regulating and herbicidal agents containing them, may be applied for instance in the form of directly sprayable solutions, powders, suspensions (including high-percentage aqueous, oily or other suspensions), dispersions, emulsions, oil dispersions, pastes dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds Ia are generally suitable for the preparation of solutions, emulsions, pastes and oil dispersions to be sprayed direct, from mineral oil fractions of medium to high boiling point, such as kerosene or diesel oil, further from coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared for active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sufonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated caster oil, polyoxytheylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredients, or growth-regulating or herbicidal agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the season, the plants to be combated and their growth stage, and varies from 0.1 to 5.0, and preferably from 0.25 to 2.0 kg/ha.

In view of the spectrum of weeds that can be combated, the tolerance of the active ingredients by crop plants, and in view of the numerous application methods available, the compounds according to the invention may, depending on their substitution pattern, be used in a large number of crops for removing unwanted plant growth. The following may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgo |
| *Spinacia oleracea* | spinach |
| *Theobroma cacao* | cacao plants |

| Botanical name | Common name |
| --- | --- |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, |

In addition to use in the above crop plants, the novel compounds may be employed to combat for example the following plants: *Abutilon theophrast, Amaranthus retroflexus, Arachis hypogaea, Avena sativa, Centraurea cyanus. Chenopodium album. Cyperus esculentus, Cyperus iria, Desmodium tortuosum, Digitaria sanguinalis, Echinochloa crus-galli, Euphorbia heterophylla, Galium aparine, Ipomoea spp, Lamium amplexicaule, Mercurialis annua, Rottboellia exaltata, Sesbania exaltata, Setaria italica, Sinapis alba, Solanum nigrum, Sorghum bicolor, Veronic spp.,* and *Viola tricolor.*

To increase the spectrum of action and to achieve synergistic effects, the thiazolo-(2,3-b)-quinazolone derivatives of the formula I may be mixed with each other or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds of the formula Ia, either along or in combination with other herbicides, in admixture with other crop protection agents, e.g. agents for combating pests or phytopathogenic fungi or bacteria. The compounds may also be mixed with solutions of mineral salts used to remedy nutritional or trace element deficiencies. Non-phytotoxic oils and oil concentrates may also be added.

MANUFACTURING EXAMPLES

EXAMPLE 1

9-chloro-5H-thiazolo-(2,3-b)-quinoazolin-5-one (compound 1)

Over a period of 35 minutes, a mixture of 34 g of 3-chloroanthranilamide and 23.9 g of 2-chlorothiazole was heated to 170° C. and stirred for 5 hours at this temperature. After the addition of a further 2.87 go of 2-chlorothiazole, the mixture was stirred for a further 5 hours at 170° C. Subsequently, a mixture of 140 ml of water and 60 ml of 25% strength ammonia solution was added at 90° C. The reaction mixture was cooled to 25° C., stirred for 10 minutes at this temperature and worked up as usual. Yield: 33.6 g (71%) of compound 1; m.p. 185°-189° C.

EXAMPLE 2

6-fluoro-5H-thiazolo-(2,3-b)-quiazoline-5-one (compound 2)

While stirring, 59.5 g of 6-fluoroanthranilamide was added to 47.4 g of 2-chlorothiazole. The reaction mixture was heated for 30 minutes at 150° C. and stirred for 5½ hours. Water was added to the reaction mixture and a pH of 9 was set up by adding 25% strength ammonia solution. Working up in the conventional manner gave 75.5 g (89%) of compound 2; m.p, 226°-228° C.

EXAMPLE 1

6-methyl-5H-thiazolo-(2,3-b)-quinazolin-5-one (compound 3)

While stirring, 22.5 g of 6-methylanthranilamide was added to 18 g of 2-chlorothiazole. The reaction mixture was heated over a 20-minute period to 140° C. and stirred for 4 hours. Water was added to the reaction mixture, and a pH of 10 was set by adding 25% strength ammonia solution. Working up in the conventional manner gave 22.3 g (69%) of compound 3; m.p. 148°-150° C.

EXAMPLE 4

2-chloro-6-methyl-5H-thiazolo-(2,3-b)-quinazolin-5-one (compound 4)

While stirring, 9.75 g of 6-methylanthranilamide was added to 10.8 g of 2,5-dichlorothiazole. The mixture was heated over a 30-minute period to 160° C., stirred for 5 hours and worked up as usual. Yield: 10.3 g (63%) of compound 4; m.p. 162°-166° C.

EXAMPLE 5

6-methylthio-5H-thiazolo-(2,3-b)-quinazolin-5-one (compound 5)

7.2 g of methylmercaptan was introduced, at 0° to +10° C., into a solution of 8.4 g of potassium hydroxide in 120 ml of methanol. While the mixture heated up to room temperature it was purged with nitrogen, and concentrated under reduced pressure, and the residue was dissolved in 100 ml of dimethylformamide. 33 g of compound 2 was added and the resultant mixture was stirred for 3 hours at 110° C. Working up in the usual manner give 27 g (73%) of compound 5; m.p. 186°-189° C.

EXAMPLE 6

6-phenoxy-5H-thiazolo-(2,3-b)-quinazolin-5-one (compound 6)

11.3 g of potassium phenolate was added to a mixture of 16.5 g of compound 2 and 100 ml of dimethylformamide, and the mixture was stirred for 3 hours at 140° C. Working up in the usual manner gave 15 (68%) of compound 6; m.p. 145°-149° C.

In a similar manner to Examples 1 to 6 the compounds given in Table 1 below were or can be prepared by this method.

EXAMPLE 7

7,9-dimethyl-5H-thiazolo-(2,3-b)-quinazolin-5-one

A mixture of 13.1 g of 3,5-dimethylanthranilamide and 13.1 g of 2-bromothiazole was heated for 30 minutes at 155° C. and stirred for 12 hours. After the mixture had cooled to 25° C., the pH was adjusted to 9 by adding water and 25% strength ammonia solution, while stirring, and the resulting solution was stirred for 10 minutes. The solution was then suction filtered and the filtrate was washed with methanol and dried, 10.5 g of the above compound was obtained; m.p. 190°-192° C. The methanol filtrate was concentrated, taken up in ethyl acetate and chromatographed over aluminum oxide. After concentration a further 4.4 g of the above compound were obtained; total yield: 81%.

EXAMPLE 8

Methyl 7-methoxy-5H-thiazolo-(2,3-b)-quinazolin-5-one-2-carboxylate 16.5 g of 5-methoxyanthranilamide and 18.64 g of methyl 2-chlorothiazole-5-carboxylate were stirred for 1½ hours at 160° C. After working up in the conventional manner 24.7 g (85%) of the above compound was obtained; m.p. 187°–192° C.

EXAMPLE 9

Methyl 7-methylthio-5H-thiazolo-(2,3-b)-quinazolin-5-one-2-carboxylate 18.2 g of 5-methylthioanthranilamide and 18.64 g of methyl 2-chlorothiazole-5-carboxylate were stirred for 45 minutes at 160° C. After working up in the conventional manner 26.6 g (87%) of the above compound was obtained: m.p. 195°–197° C.

EXAMPLE 10

2-bromo-6-chloro-5H-thiazolo-(2,3-b)-quinazolin-5-one 11.1 g of chloroanthanilamide and 15.8 g of 2,5-dibromothiazole were stirred for 2 hours at 140° C. After working up in the conventional manner there was obtained 16.4 g (80%) of the above compound; m.p. 174°–178° C.

EXAMPLE 11

8-methyl-5H-thiazolo-(2,3-b)-quinazolin-5-one 15 g of 5-methylantranilamide and 12 g of 2-chlorothiazole were stirred for 1 hour at 140° C. After working up in the conventional manner there was obtained 17.9 g (83%) of the above compound; m.p. 174°–178° C.

EXAMPLE 12

2-methyl-6-chloro-5H-thiazolo-(2,3-b)-quinazolin-5-one (compound 14)

10.2 g of 6-chloroanthranilamide and 10.74 g of 2-bromo-5-methylthiazole were stirred at 140° C. for 2 hours. After working up in the conventional manner there was obtained 11.7 g (78%) of the above compound; m.p. 235°–236° C.

EXAMPLE 13

9-methoxy-5H-thiazolo-(2,3-b)-quinazolin-5-one (compound 48)

16.6 g of 3-methoxyanthranilamide and 16.4 g of 2-bromothiazole were stirred for 7 hours at 150° C. After working up in the conventional manner there was obtained 20.2 g (87%) of the above compound; m.p. 230°–232° C.

EXAMPLE 14

2-bromo-3-methyl-9-methoxy-5H-thiazolo-(2,3-b)-quinazolin-5-one (compound 80)

4.8 g of 3-methoxyanthranilamide and 7.5 g of 2,5-dibromo-4-methylthiazole were stirred for 12 hours at 140° C. After working up in the conventional manner there was obtained 7.3 g (77%) of the above compound; m.p. 198°–199° C.

EXAMPLE 15

3-methyl-6-trifluoromethyl-5H-thiazolo-(2,3-b)-quinazolin-5-one (compound 61)

12.7 g of 6-trifluoromethylantranilamide and 8.27 g of 2-chloro-4-methylthiazole were stirred for 8 hours at 140° C. After working up in the conventional manner there was obtained 13.5 g (77%) of the above compound; m.p. 182°–186° C.

EXAMPLE 16

Ethyl 6-chloro-5H-thiazolo-(2,3-b)-quinazolin-5-one-carboxylate 10.2 g of 6-chloroanthanilamide and 14.2 g of ethyl 2-bromothiazole-4-carboxylate were stirred for 10 hours at 140° C. After working up in the conventional manner there was obtained 13.3 g (72%) of the above compound; m.p. 157°–160° C.

EXAMPLE 17

9-fluoro-5H-thiazolo-(2,3-b)-quinazolin-5-one (compound 9)

15.4 g of 3-fluoroanthranilamide and 13.1 g of 2-chlorothiazole were stirred for 7 hours at 150° C. After working up in the conventional manner there was obtained 17.3 g (79%) of the above compound; m.p. 187°–189° C.

EXAMPLE 18

2,3,6-trimethyl-5H-thiazolo-(2,3-b)-quinazolin-5-one (compound 71)

9.6 g of 6-methylanthranilamide and 12.6 g of 2-bromo-4,5-dimethylthiazole were stirred for 12 hours at 150° C. After working up in the conventional manner there was obtained 11.9 g (81%) of the above compound; m.p. 278°–280° C.

EXAMPLE 19

2-methyl-6-fluoro-5H-thiazolo-(2,3-b)-quinazolin-5-one (compound 59)

10.8 g of 6-fluoroanthranilamide and 9.4 g of 2-chloro-5-methylthiazole were stirred for 7 hours at 150° C. After working up in the conventional manner there was obtained 13.5 g (83%) of the above compound; m.p. 245°–246° C.

EXAMPLE 20

Methyl 5H-thiazolo-(2,3-b)-quinazolin-5-one-8-carboxylate 19.4 g of 4-carbomethoxyanthranilamide and 12 g of 2-chlorothiazole were stirred for 4 hours at 150° C. After working up in the conventional manner there was obtained 20.3 g (78%) of the above compound; m.p. 228°–230° C.

TABLE 1

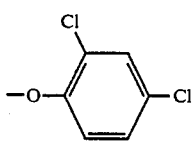

(I)

| Compound No. | R¹ | R² | R³ | R⁴ | mp. [°C.] |
|---|---|---|---|---|---|
| 7 | H | H | Cl | H | 213–215 |
| 8 | H | H | Br | H | 205–207 |
| 9 | H | H | H | F | 187–189 |
| 10 | H | H | H | Br | 183–184 |
| 11 | H | H | Cl | Cl | 192–196 |
| 12 | H | H | H | $CH_3$ | 180–184 |
| 13 | H | $CH_3$ | Cl | H | 274–277 |
| 14 | $CH_3$ | H | Cl | H | |
| 15 | H | $CH_3$ | H | F | |
| 16 | $CH_3$ | H | H | F | |
| 17 | H | $CH_3$ | H | $CH_3$ | 188–190 |
| 18 | $CH_3$ | H | H | $CH_3$ | |
| 19 | H | $CH_3$ | $CH_3$ | H | 217 decomp. |
| 20 | H | $CH_3$ | Br | H | 260–261 |
| 21 | $CH_3$ | H | $OCH_3$ | H | 203–206 |
| 22 | Cl | H | $OCH_3$ | H | |
| 23 | H | $CH_3$ | $OCH_3$ | H | 222–224 |
| 24 | Cl | Cl | $OCH_3$ | H | |
| 25 | Cl | Cl | Cl | H | |
| 26 | Cl | Cl | F | H | |
| 27 | Cl | Cl | $CH_3$ | H | |
| 28 | Cl | Cl | H | $CH_3$ | |
| 29 | Cl | Cl | H | Cl | |
| 30 | Cl | Cl | H | $OCH_3$ | |
| 31 | Cl | Cl | H | F | |
| 32 | Cl | H | H | $OCH_3$ | |
| 33 | H | $CH_3$ | H | $OCH_3$ | 206–210 |
| 34 | Cl | Cl | H | $OCH_3$ | |
| 35 | H | H | $CH_3$ | $CH_3$ | |
| 36 | H | H | Cl | $CH_3$ | 173–175 |
| 37 | H | H | $CH_3$ | Cl | |
| 38 | H | $CH_3$ | Cl | $CH_3$ | |
| 39 | H | $CH_3$ | Cl | Cl | |
| 40 | Cl | H | Cl | Cl | |
| 41 | H | $CH_3$ | $CH_3$ | H | |
| 42 | Cl | H | S—$CH_3$ | H | |
| 43 | H | H | O—Et | H | 145–147 |
| 44 | H | $CH_3$ | O—Et | H | 163–165 |
| 45 | H | H | O-i-$C_3H_7$ | H | 92–96 |
| 46 | H | H | H | O—Et | |
| 47 | H | $CH_3$ | H | O—Et | |
| 48 | H | H | H | O—$CH_3$ | 230–232 |
| 49 | H | H | O—$CH_3$ | H | 162–166 |
| 50 | H | H | S—$C_6H_5$ | H | |
| 51 | H | H | 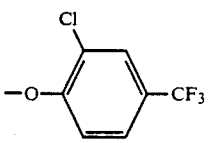 | H | |
| 52 | H | H | 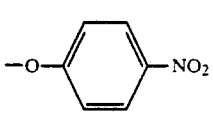 | H | |
| 53 | H | H | 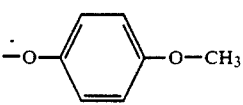 | H | |
| 54 | H | H |  | H | |

TABLE 1-continued

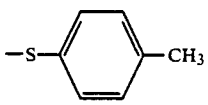

(I)

| Compound No. | R¹ | R² | R³ | R⁴ | mp. [°C.] |
|---|---|---|---|---|---|
| 55 | H | H | ![-S-C6H4-CH3] | H | |
| 56 | H | H | ![-S-C6H3(Cl)-Cl] | H | |
| 57 | H | CH₃ | CO₂H | H | 258 decomp. |
| 58 | CH₃ | H | H | CH₃ | 155–158 |
| 59 | CH₃ | H | F | H | 245–246 |
| 60 | Br | H | H | H | 161–165 |
| 61 | H | CH₃ | CF₃ | H | 182–186 |
| 62 | H | H | CF₃ | H | |
| 63 | H | H | H | CF₃ | |
| 64 | H | CH₃ | H | Cl | 228–230 |
| 65 | CH₃ | H | CH₃ | H | 185–187 |
| 66 | Br | CH₃ | CH₃ | H | 148–150 |
| 67 | Br | CH₃ | Cl | H | 196–198 |
| 68 | Br | CH₃ | H | CH₃ | 183–184 |
| 69 | Br | CH₃ | H | Cl | |
| 70 | Cl | CH₃ | Cl | H | |
| 71 | CH₃ | CH₃ | CH₃ | H | 278–280 |
| 72 | CH₃ | CH₃ | Cl | H | 224–225 |
| 73 | CH₃ | CH₃ | H | CH₃ | 175–178 |
| 74 | CH₃ | CH₃ | H | Cl | |
| 75 | CH₃ | CH₃ | F | H | |
| 76 | CH₃ | CH₃ | OCH₃ | H | 201–204 |
| 77 | OCH₃ | H | H | H | |
| 78 | OCH₃ | H | Cl | H | |
| 79 | OCH₃ | H | H | CH₃ | |
| 80 | Br | CH₃ | H | OCH₃ | 198–199 |
| 81 | CH₃ | CH₃ | H | OCH₃ | 187–189 |
| 82 | Br | H | CH₃ | H | 191–195 |

USE EXAMPLES

The herbicidal action of the thiazolo-(2,3-b)-quinazolones of the formula Ia on the growth of test plants was demonstrated in the greenhouse experiments described below.

The vessels employed were plastic flowerpots having a volume of 300 cm³, and which were filled with a sandy loam containing about 3.0% humus. The seeds of the test plants were sown shallow, and separately, according to species.

For the preemergence treatment, the active ingredients were applied to the surface of the soil immediately after the seeds had been sown. The compounds were emulsified or suspended in water as vehicle, and sprayed through finely distributing nozzles. The application rate was 3.0 kg/ha. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients, and prevented readily volatile substances from evaporating.

For the postemergence treatment, either plants which had been sown directly in the pots and grown there were selected, or plants which had been grown from seedlings and transplanted to the vessels a few days before treatment.

Depending on growth form, the plants were grown to a height of from 3 to 15 cm before being treated with the active ingredients (suspended or emulsified in water as vehicle and sprayed through finely distributing nozzles). The application rates for postemergence treatment varied from 0.1 to 5, and preferably from 0.25 to 2, kg/ha.

The pots were set up in the greenhouse—species from warmer areas at from 20° to 35° C., and species from moderate climates at 10° to 20° C. The experiments were run for 2 to 4 weeks. During this period the plants were tended and their reactions to the various treatments assessed.

On preemergence application of 3.0 kg/ha, compound 12 had a good action on unwanted plants such as *Echinochloa crus-galli*, *Galium aparine* and *Ipomoea spp.* were well controlled by postemergence application of compounds 12, 23 and 49.

Compounds 12, 49, 33 and 9 had, on postemergence application of 3.0 kg/ha, a good action on perennial Cyperaceae such as *Cyperus esculentus*.

Compound 43 exhibited, on postemergence application of only low rates, a considerable herbicidal action on a number of unwanted plants such as *Amaranthus retroflexus, Chenopodium album, Euphorbia heterophylla, Galium aparine, Ipomoea spp., Mercurialis annua, Sesbania exaltata* and *Solanum bicolor*.

Compound 33, applied postemergence, proved extremely suitable for combating grassy plants such as *Digitaria sanguinalis, Setaria italica* and *Sorghum bicolor*. The crop plant wheat was only slightly damaged, if at all; the action was selective.

The crop plant Indian corn remained completely uninfluenced by compound 9, whereas unwanted plants selected at random, such as *Cyperus iria* and *Solanum nigrum*.

Compounds 17 and 43, applied postemergence at a rate of 0.125 kg/ha, combated broadleaved weeds, without causing any appreciable damage to the crop plant Indian corn.

At 0.25 kg/ha, compound 3 selectively combated weeds in groundnuts. At the same rate, compound 71 combated broadleaved unwanted plants in winter wheat.

Heavy damage was caused to unwanted plants by compound 2 at 0.5 kg/ha, and phytotoxicity in oats, wheat and Indian corn was low.

Applied postemergence at a rate of 0.125 kg/ha, compound 9 selectively combated unwanted broadleaved plants in wheat.

Broadleaved and grassy unwanted plants were controlled by compound 5 at a rate of 0.25 kg/ha, the crop plants wheat and Indian corn suffering at most temporary and acceptable damage.

We claim:

1. A process for the manufacture of thiazolo-(2,3-b)-quinazolones of the formula I

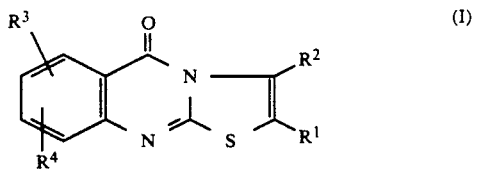

where $R^1$, $R^2$, $R^3$ and $R^4$ are each hydrogen, halogen, nitro, cyano, alkyl, haloalkyl, cycloalkyl, alkoxy, alkylthio, alkanoylamino, haloalkanoylamino, carboxyl, carbamoyl, dialkylcarboxamido, alkoxycarbonylalkyl, unsubstituted or alkoxy-substituted alkoxycarbonyl, alkylsulfonyl, phenylsulfonyl, sulfamoyl, alkylaminosulfonyl, alkylsulfonylamino, unsubstituted or halogen-, alkyl-, haloalkyl-, nitro-or alkoxy-substituted phenyl, phenoxy or thiophenyl, or unsubstituted or halogen- or alkyl-substituted hetrayl, wherein either a) an anthranilamide derivative of the general formula II

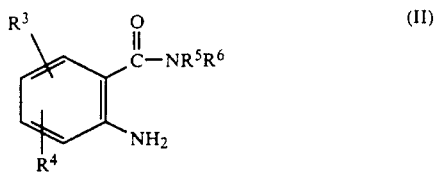

where $R^5$ and $R^6$ are hydrogen or $C_1$–$C_4$-alkyl, is reacted with a thiazole derivative of the formula III

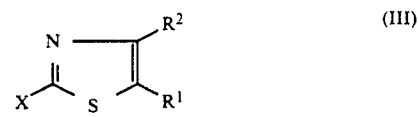

where X is fluorine, chlorine, bromine, alkylsulfonyl or arylsulfonyl, b) for certain radicals $R^{4'}$ from the group $R^4$—a thiazolo-(2,3-b)-quinazolone of the general formula IV

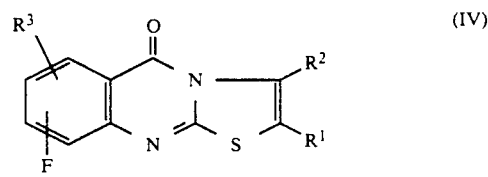

is reacted with a nucleophile $R^{4'}$-M, where $R^{4'}$ is alkoxy, alkylthio or unsubstituted or halogen-, alkyl-, haloalkyl-, nitro- or alkoxy-substituted phenoxy or thiophenyl and M is hydrogen, or an alkali metal, alkaline earth metal or ammonium cation.

2. The process of claim 1, wherein the reaction is carried out at from 100° to 200° C.

3. The process of claim 1, wherein an anthranilamide derivative of the formula IIa

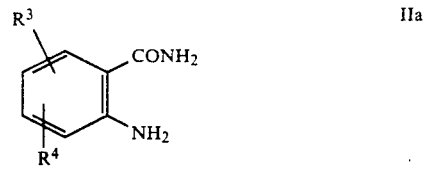

is reacted with the thiazaole derivative III.

4. The process of claim 1, wherein an anthranilamide derivative II is reacted with a thiazole derivative of the formula IIIa

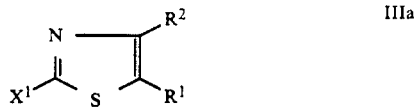

where $X^1$ is chlorine or bromine.

5. The process of claim 1, wherein the reaction is carried out in a melt.

6. The process of claim 1, wherein the reactants are used in a molar ratio of from 0.85 to 1.2.

* * * * *

UNITED STATES PATENT AND TRADEMARK OFFICE
CERTIFICATE OF CORRECTION

PATENT NO. : 5,030,727
DATED : July 9, 1991
INVENTOR(S) : Gerhard HAMPRECHT et al.

It is certified that error appears in the above-identified patent and that said Letters Patent is hereby corrected as shown below:

On the title page and col. 1-2.

Title:
That part reading "ZUINAZOLONES" should read
-- Quinazolones --

Inventors:
That part reading "Guenther Seybold, Neuhoren" should read -- Guenther Seybold, Neuhofen --

Signed and Sealed this

First Day of December, 1992

Attest:

DOUGLAS B. COMER

Attesting Officer

Acting Commissioner of Patents and Trademarks